United States Patent [19]

Suzuki

[11] 4,221,921
[45] Sep. 9, 1980

[54] MONOCHLOROACETIC ACID FROM HYDROXYACETIC ACID

[75] Inventor: Shigeto Suzuki, San Francisco, Calif.

[73] Assignee: Chevron Research Company, San Francisco, Calif.

[21] Appl. No.: 904,670

[22] Filed: May 10, 1978

Related U.S. Application Data

[63] Continuation of Ser. No. 735,650, Oct. 26, 1976, abandoned.

[51] Int. Cl.$^2$ .................... C07C 51/00; C07C 53/16
[52] U.S. Cl. .................................. 562/603; 203/49; 560/226
[58] Field of Search ..................... 260/531 R; 562/603

[56] References Cited

FOREIGN PATENT DOCUMENTS 1486033  6/1967  France .................................. 260/531 R Primary Examiner—Vivian Garner
Attorney, Agent, or Firm—D. A. Newell; John Stoner, Jr.; A. T. Bertolli

[57] ABSTRACT

A process for producing monochloroacetic acid from hydroxyacetic acid which comprises feeding hydroxyacetic acid and aqueous hydrogen chloride to a reaction zone and contacting the hydroxyacetic acid with the aqueous hydrogen chloride in the presence of hydrogen iodide catalyst at a temperature between 100° and 250° C. and a pressure sufficient to maintain the aqueous hydrogen chloride in liquid phase. Preferably the reaction is carried out at a temperature between about 130° and 200° C.

6 Claims, No Drawings

MONOCHLOROACETIC ACID FROM HYDROXYACETIC ACID

CROSS-REFERENCE TO RELATED APPLICATION

This application is a continuation-in-part of U.S. application Ser. No. 735,650, filed Oct. 26, 1976, now abandoned.

BACKGROUND OF THE INVENTION

The present invention relates to the production of monochloroacetic acid from hydroxyacetic acid.

Monochloroacetic acid has long been made by chlorinating acetic acid in the presence of a catalyst and removing from the monochlorinated product dichloroacetic acid and other by-products of the reaction. It is well known that these operations are difficult to accomplish economically in a manner yielding a product of satisfactory purity. The chlorination is usually carried out by passing chlorine into a mixture of glacial acetic acid and acetic anhydride and/or acetyl chloride while heating the mixture under reflux at a reaction temperature, usually from 80° to 110° C., and venting the gaseous hydrogen chloride which is formed. After completing the reaction, the monochloroacetic acid product is crystallized and then subjected to recrystallization and/or solvent extraction operations to remove impurities, especially dichloroacetic acid, down to a point at which the monochloroacetic acid is of a purity acceptable on the market. The dichloroacetic acid boils at close to the same temperature as monochloroacetic acid and cannot satisfactorily be removed by distillation.

The present invention provides a process for producing monochloroacetic acid in such a manner that it is relatively easily separated by distillation from the reaction zone effluent.

According to U.S. Pat. No. 2,503,334, conversion of acetic acid to monochloroacetic acid by chlorination can be carried out in the presence of iodine catalyst.

Other processes which have been disclosed for producing monochloroacetic acid include that of U.S. Pat. No. 935,606, wherein dichloroethoxyethylene is hydrolyzed to monochloroacetic acid and ethanol; and also that of U.S. Pat. No. 2,298,138, which states that chloroacetic acid can be produced by the reaction of formaldehyde with carbon monoxide and hydrogen chloride.

The reaction of primary alcohols with hydrogen chloride in the presence of catalyst is disclosed, for example in U.S. Pat. No. 3,484,494 (vapor-phase reaction of alkanol with hydrogen chloride in the presence of alumina-potassium catalyst) and in Morrison and Boyd, Organic Chemistry, Allyn and Bacon, 1970, page 525 (zinc chloride catalyst).

SUMMARY OF THE INVENTION

The present invention provides a process for producing monochloroacetic acid from hydroxyacetic acid which comprises feeding hydroxyacetic acid and aqueous hydrogen chloride to a reaction zone and contacting the hydroxyacetic acid with the aqueous hydrogen chloride in the presence of hydrogen iodide catalyst at a temperature between 100° and 250° C. and a pressure sufficient to maintain the aqueous hydrogen chloride in liquid phase.

The present invention is based on my finding that hydroxyacetic acid is converted to monochloroacetic acid by contact with aqueous hydrogen chloride under conditions of moderate temperature, namely 100°–250° C. to give surprisingly clean yields of monochloracetic acid as opposed to a mixture of mono-, di- and trichloroacetic acid. Thus, an important advantage of the present process is that the monochloroacetic acid can be readily separated from the hydroxyacetic acid by distillation. The separated hydroxyacetic acid is advantageously recycled to the monochloroacetic acid production reaction zone. Prior to the separation of the hydroxyacetic acid-monochloroacetic acid by distillation, the hydrogen chloride and water are separated from the reaction zone effluent by stripping-distillation. The overhead from the stripping operation is hydrogen chloride and water, which can be recycled to the reaction zone. The bottoms from the stripping operation is the hydroxyacetic acid and monochloroacetic acid.

I have found that the present reaction of hydroxyacetic acid to monochloroacetic acid is surprisingly sensitive to temperature. At 130° C. I have obtained conversions of about 7%, whereas at 180° C. I obtained conversion of hydroxyacetic acid to monochloroacetic acid of about 40% by weight.

Accordingly, preferred temperature for the reaction of the present invention is between about 130° and 200° C.

I have found that hydrogen iodide has a catalytic effect on the reaction of hydroxyacetic acid with the aqueous hydrogen chloride. Accordingly, the conversion of hydroxyacetic acid to monochloroacetic acid is carried out in the presence of about 0.0001 to 1.0 mol of hydrogen iodide per mol of hydroxyacetic acid feed to the reaction zone.

The aqueous hydrogen chloride used in the present process contains a substantial amount of water, at least about 20 weight percent water. Preferably the aqueous hydrogen chloride is 10-60 weight percent hydrogen chloride and the balance water, more preferably 20-40% hydrogen chloride. Preferably the weight ratio of parts hydrogen chloride in the aqueous hydrogen chloride feed to parts hydroxyacetic acid in the feed is between 1:1 and 10:1.

The reaction is carried out under sufficient pressure to maintain the aqueous hydrogen chloride in liquid phase although, of course, there will be an equilibrium amount of the hydrogen chloride and water in the vapor phase. Suitable pressures are generally between about 10 psig and 10,000 psig, preferably between about 50 psig and 5000 psig.

TABLE I

| | Operating Conditions | |
|---|---|---|
| | Preferred | More Preferred |
| HCl/glycolic acid ratio (by weight) | 1:1 to 20:1 | 3:1 to 10:1 |
| Aqueous HCl conc. (wt. %) | 10 to 60% | 20 to 40% |
| Temperature | 100° to 250° C. | 130° to 200° C. |
| Pressure (psig) | 10 to 10,000 | 50 to 5000 |
| Reaction time (minutes) | 15 to 240 | 30 to 120 |
| HI/glycolic acid (mol ratio) | 0.0001:1 to 1:1 | 0.001:1 to 0.05:1 |

Table I above shows preferred and more preferred operating conditions for the process of the present invention.

EXAMPLES

EXAMPLE 1

A glass pressure bottle was charged with 8 g. (0.1 mol) of 95 weight percent glycolic acid and 37 weight percent aqueous hydrogen chloride (containing 0.6 mol hydrogen chloride), and the mixture was stirred at 127°–129° C. for 2.1 hours. The maximum pressure reached was 117 psig. Excess aqueous hydrogen chloride was removed from the product mixture by distillation, and the residue was methylated by refluxing with excess methanol. The gas chromatographic analysis of the methylated product showed that the conversion of glycolic acid was 7% and the yield of monochloroacetic acid was over 90 mol percent.

EXAMPLE 2

A mixture of 0.5 g (0.0066 mol) glycolic acid, 2.0 g of 37 weight percent aqueous hydrogen chloride (containing 0.020 mol hydrogen chloride) and 0.026 g (0.0002 mol) hydrogen iodide was sealed in two glass ampules. The first ampule was heated at 130° C. for 2 hours and the second at 130° C. for 4 hours. The analysis of both ampule contents showed respective glycolic acid conversions of 14 mol percent in the ampule heated for 2 hours and 27 mol percent in the ampule heated for 4 hours, with chloroacetic acid yields of over 95 mol percent in both cases.

What is claimed is:

1. A process for producing monochloroacetic acid from hydroxyacetic acid which comprises feeding hydroxyacetic acid and aqueous hydrogen chloride to a reaction zone and contacting the hydroxyacetic acid with the aqueous hydrogen chloride in the presence of 0.0001 to 1.0 mol hydrogen iodide per mol of hydroxyacetic acid at a temperature between 100° and 250° C. and a pressure sufficient to maintain the aqueous hydrogen chloride in liquid phase.

2. A process in accordance with claim 1 wherein the temperature is between 130° and 200° C.

3. A process in accordance with claim 1 wherein the aqueous hydrogen chloride fed to the reaction zone is between 10 and 60 weight percent hydrogen chloride.

4. A process in accordance with claim 3 wherein the ratio of parts aqueous hydrogen chloride to parts hydroxyacetic acid in the feed is between 1:1 and 10:1 by weight.

5. A process in accordance with claim 1 wherein the aqueous hydrogen chloride fed to the reaction zone is between 20 and 40 weight percent hydrogen chloride.

6. A process in accordance with claim 1 wherein the contacting is carried out in the presence of 0.001 to 0.05 mol hydrogen iodide per mol of hydroxyacetic acid feed to the reaction zone.

* * * * *